United States Patent
Ahn et al.

(10) Patent No.: US 7,642,056 B2
(45) Date of Patent: Jan. 5, 2010

(54) METHOD AND KIT FOR DETECTING A TARGET PROTEIN USING A DNA APTAMER

(75) Inventors: Dae-Ro Ahn, Seoul (KR); Eun Gyeong Yang, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 12/047,731

(22) Filed: Mar. 13, 2008

(65) Prior Publication Data

US 2008/0261225 A1    Oct. 23, 2008

(30) Foreign Application Priority Data

Mar. 14, 2007    (KR)    ............. 10-2007-0025105

(51) Int. Cl.
   *C12Q 1/68*    (2006.01)
(52) U.S. Cl. ........................................... 435/6
(58) Field of Classification Search ............... None
   See application file for complete search history.

(56) References Cited

U.S. PATENT DOCUMENTS 6,680,377 B1    1/2004    Stanton et al.

2005/0089864 A1    4/2005    Li et al.
2006/0257914 A1    11/2006    Bruno et al.
2007/0231810 A1 *    10/2007    Todd et al. .............. 435/6

FOREIGN PATENT DOCUMENTS

| WO | WO 01/57259 A1 | 8/2001 |
| WO | WO 02/34935 A2 | 5/2002 |
| WO | WO 2005052127 A2 * | 6/2005 |

* cited by examiner

Primary Examiner—Young J Kim
(74) Attorney, Agent, or Firm—Sughrue Mion, PLLC

(57) ABSTRACT

A method and a kit for detecting a target protein in a sample with a signal amplification strategy are provided. The signal amplification strategy is established for the aptamer-based molecular recognition of a target protein with concomitant release of single-stranded DNA (G-DNA), which binds complementarily to a single-stranded RNA comprising a fluorophore and a quencher ("F-RNA-Q"). The fluorescence-quenched RNA is then degraded by RNase H to result in a fluorescence signal, and the undamaged G-DNA is recycled to yield fluorescence amplification.

11 Claims, 3 Drawing Sheets

METHOD AND KIT FOR DETECTING A TARGET PROTEIN USING A DNA APTAMER

This is a non-provisional application which claims priority from Korean patent application 10-2007-0025105 filed on Mar. 14, 2007, which is incorporated herein by reference.

FIELD OF THE INVENTION

The present invention relates to a method and a kit for analyzing a target protein contained in a sample.

BACKGROUND OF THE INVENTION

Aptamers are nucleic acid species that are routinely selected in vitro through SELEX (systematic evolution of ligands by exponential enrichment). Since their introduction by the Gold and Szostak groups (Tuerk and Gold, *Science*, vol. 249, pp. 505-510, (1990)), aptamers have been exploited as molecular-recognition elements to detect virtually any target of interest, ranging from small molecules to proteins to even cells and tissues. Aptamers, which rival antibodies in sensitivity and specificity, are readily reproduced by chemical synthesis with low cost. Furthermore, they possess desirable storage properties and elicit little or no immunogenicity in a biological context. Owing to their advantages in comparison to antibodies, their utility in therapeutics and diagnostics has significantly expanded. Recently, the lack of inherent signaling properties of aptamers has prompted development of various strategies for transducing target-binding events into readily measurable signals for biotechnological and biomedical applications (Navani and Li, *Curr. Opin. Chem. Biol.*, vol. 10, pp. 272-281 (2006)).

Methods that employ fluorescent reporters have proven to be particularly useful in generation of aptamer-based biosensors; these include monochromophore approaches (Jhaveri et al., *J. Am. Chem. Soc.*, vol. 122, pp. 2469-2473 (2000)), aptamerbeacon engineering (Hamaguchi et al., *Anal. Biochem.*, vol. 294, pp. 126-131 (2001)), structure-switching signaling (Nutiu and Li, *J. Am. Chem. Soc.*, vol. 125, pp. 4771-4778 (2003)), in situ labeling (Merino and Weeks, *J. Am. Chem. Soc.*, vol. 125, pp. 12370-12371 (2003)), allosteric chimeras (Wu and Curran, *Nucleic Acids Res.*, vol. 27, pp. 1512-1516 (1999)), dye-staining approaches (Li et al., *Chem. Commun.*, pp. 73-75 (2007)), and polymer-conjugate based fluorescent chemosensors (Ho and Leclerc, *J. Am. Chem. Soc.*, vol. 126, pp. 1384-1387 (2004)). While these systems generally produce signals in a stoichiometric manner, attempts have been made to amplify signals by incorporation of a proximity-ligation assay (Fredriksson et al., *Nature Biotechnol.*, vol. 20, pp. 473-477 (2002)) or an exonuclease-protection assay (Wang et al., *Anal. Chem.*, vol. 76, pp. 5605-5610 (2004)) into aptamer-based sensing. Although ultrasensitive detection of proteins has been achieved, the former assay is limited to homodimer protein targets, and the latter assay suffers from tedious multistep procedures. Very recently, a DNA-polymerase assay integrated with a molecular beacon has been employed for the amplified detection of the recognition between aptamer and target small molecule (Shlyahovsky et al., *J. Am. Chem. Soc.*, vol. 129, pp. 3814-3815 (2007)). Such techniques are in continuous demand for developing simple and easily applicable aptamer-based methods that can facilitate accurate and specific bioanalysis.

SUMMARY OF THE INVENTION

In a first aspect, the present invention is a method of detecting a target protein by amplifying the fluorescence signal generated as a DNA aptamer binds a target protein in the presence of other molecules in a sample. The method comprises the steps of:

1) forming a DNA duplex consisting of (a) a DNA aptamer (5'-Ex_aptamer) comprising a sequence needed for target binding and a sequence extended from the 5'-end of the target binding sequence and (b) a single stranded DNA (Guard-DNA or G-DNA) complementary to a region of the DNA aptamer that includes the 5'-extended region;

2) mixing the sample containing the target protein with the DNA duplex of step 1);

3) mixing the mixture obtained in step 2) with RNase H and a single-stranded RNA (F-RNA-Q) complementary to the G-DNA, wherein a fluorophore and a quencher are labeled at the 5'- and 3'-ends, respectively, of the single-stranded RNA; and 4) measuring the fluorescence intensity of the mixture obtained in step 3).

In a second aspect, the present invention is a kit providing a method of detecting a target protein in a sample. The kit comprises: 1) a DNA duplex consisting of (a) a DNA aptamer and (b) a single-stranded DNA complementary to a region of the DNA aptamer that includes the 5'-extended region; 2) a single-stranded RNA complementary to the G-DNA and labeled with a fluorophore and a quencher; and 3) RNase H.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

Figure 1:
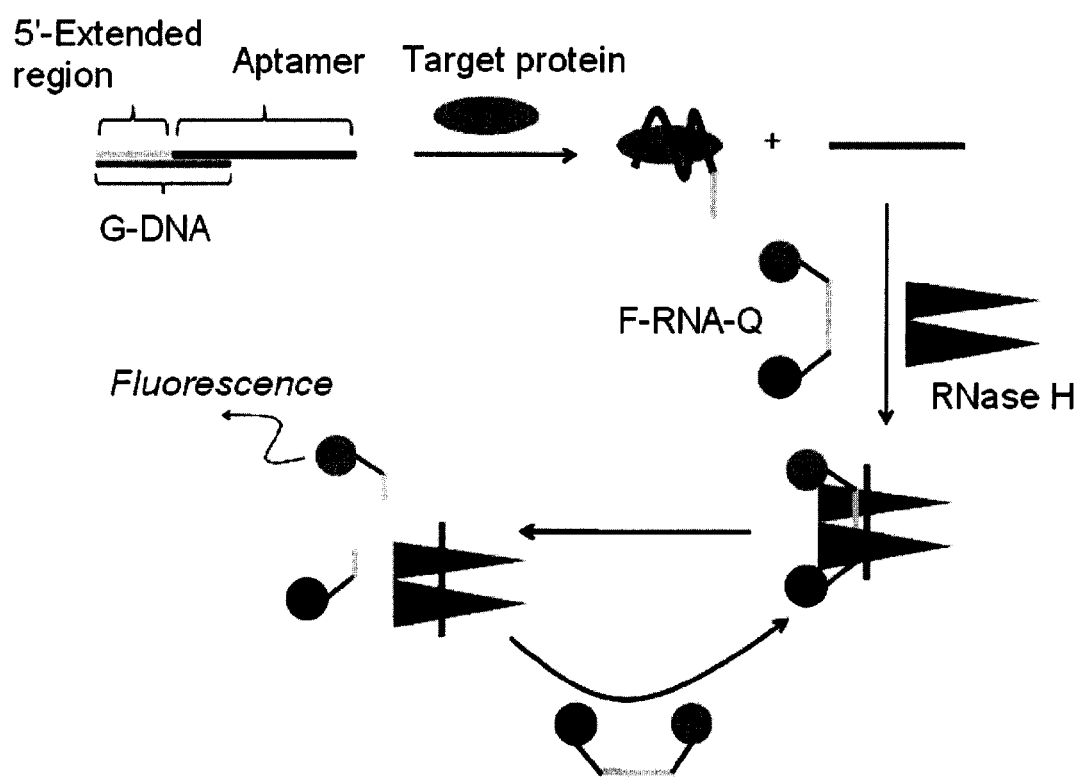
FIG. 1 is a schematic illustration showing the principle on which the present invention is based.

The present invention relates to a biosensor based on fluorescence intensity assay which is used in measurement of a target protein in a sample and characteristically comprises the steps of:

1) forming a DNA duplex consisting of (a) a DNA aptamer (5'-Ex_aptamer) comprising a sequence needed for target binding and a sequence extended from the 5'-end of the target binding sequence and (b) a single stranded DNA (Guard-DNA or G-DNA) complementary to a region of the DNA aptamer that includes the 5'-extended region;

2) mixing the sample containing the target protein with the DNA duplex of step 1);

3) mixing the mixture obtained in step 2) with RNase H and a single-stranded RNA (F-RNA-Q) complementary to the G-DNA, wherein a fluorophore and a quencher are labeled at the 5'- and 3'-ends, respectively, of the single-stranded RNA; and 4) measuring the fluorescence intensity of the mixture obtained in step 3).

The DNA aptamer of step 1) is a molecule having an extended sequence at the 5'-end of an established aptamer (5'Ex_aptamer). The G-DNA in this embodiment is a single-stranded DNA molecule complementary to a region of the DNA aptamer that includes the 5'-extended region. The established aptamer is an aptamer which binds to a target protein. A DNA duplex consisting of the DNA aptamer and the G-DNA may be formed by heating an aqueous solution containing the DNA aptamer and the G-DNA and slowly cooling at room temperature.

The target protein of step 2), which may be a protein, includes, but not limited to, an antibody, a ligand, a natural compound, an extract, a synthetic peptide, a candidate compound for a new drug, or a protein.

The F-RNA-Q of step 3) is an RNA sequence that has a fluorophore attached at its 5'-end and a quencher attached at its 3'-end. In preferred embodiments, the fluorophore is a conventional fluorescent material such as fluorescein, tetramethylrhodamine, Cy5, Cy3, and Texas Red. In preferred embodiments, the quencher may be a conventional one such as dabsyl, dabcyl, and a black quencher. The quencher may be another fluorophore acting as a fluorescence acceptor in fluorescence resonance energy transfer (FRET) mechanism. Any of more fluorophore and fluorescence quencher known to a skilled person in the relevant art may be used in the present invention.

RNase H of this embodiment is an enzyme which recognizes a RNA/DNA double strand and degrades only the RNA part of the double strand, but does not degrade a single-stranded RNA. In the present invention, RNase H is used to degrade F-RNA-Q of the F-RNA-Q/G-DNA double strand.

The DNA aptamer, the G-DNA, F-RNA-Q and RNase H used in the present invention may be commercially available.

In step 4), the fluorescence intensity may be measured by a fluorometer known to a skilled person in the relevant art, such as TRIAD Multimode Detector, Wallac/Victor Fluorescence and Perkin-Elmer LB50B luminescence spectrometer.

The method of the present invention for detecting a target protein in a sample is explained below in more details.

In step 2), in the presence of a target protein, the 5'Ex_aptamer-containing complex of a partially double-stranded structure prefers to form the protein-5'Ex_aptamer complex; this results in the release of the single-stranded G-DNA molecule. In step 3), the biosensor system of this embodiment includes a single stranded RNA probe, F-RNA-Q, which is appended with a fluorophore (F) at the 5'-end. The intensity of this fluorophore is completely reduced by a quencher (Q) at the 3'-end. The RNA-DNA duplex is then formed since the sequence of F-RNA-Q is complementary to the released G-DNA. The RNA-DNA duplex, in which fluorescence is quenched, is degraded with RNase H; this results in a fluorophore-containing RNA fragment separated from the quencher, and was used for generating a fluorescence signal (FIG. 1). In case when the target protein does not exist in a sample, the fluorescence signal is not generated as the DNA aptamer remains bound to the G-DNA and is unable to form a RNA-DNA duplex with F-RNA-Q. Since F-RNA-Q degradation by RNase H leaves the G-DNA undamaged and thus available for duplex reformation with another F-RNA-Q molecule, the cycle of RNA-DNA duplex formation followed by RNase H digestion results in a mechanism of fluorescence signal amplification.

Figure 2:
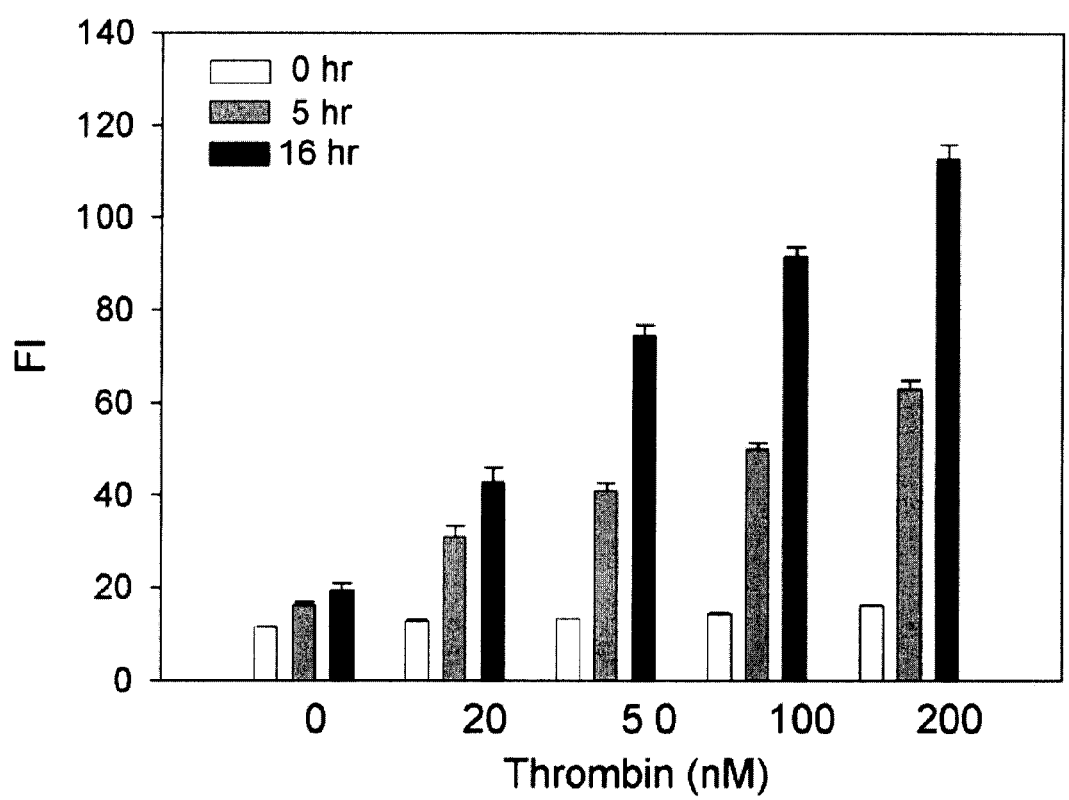
FIG. 2 is a graph showing fluorescence intensity values measured to detect and quantify α-thrombin in a buffer in accordance with the present invention. The fluorescence intensity was measured with varying concentrations of α-thrombin and/or the incubation time after treatment with RNase H and F-RNA-Q.

Furthermore, the present invention may be used for quantitative analysis of a target protein because the intensity of a fluorescence signal increases in proportion to the amount of the target protein (FIG. 2). Meanwhile, if F-RNA-Q is much longer than the G-DNA, the G-DNA and F-RNA-Q may form a double strand so that the catalytic action of RNase H may be induced even when the target protein does not exist in a sample, generating a false-positive signal. Therefore, the length of the single-stranded RNA is not longer than that of the G-DNA. When the amount of G-DNA is higher than that of the DNA aptamer, the excess G-DNA left after binding to the DNA aptamer may bind to F-RNA-Q, and RNase H may be activated to generate a false-positive signal. Therefore, the DNA aptamer and the G-DNA are preferably used in same amounts in the inventive method.

Since the method of the present invention is performed in a homogeneous solution, it is more convenient compared with ELISA (enzyme-linked immunosorbent assay) performed with additional washing steps.

Figure 3:
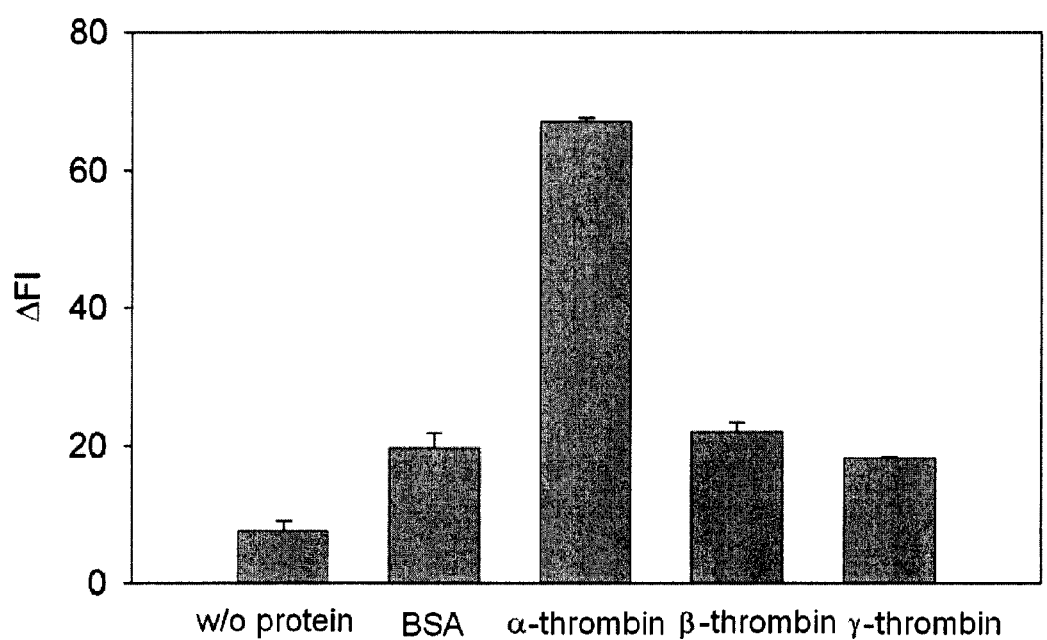
FIG. 3 is a graph showing specificity of the thrombin aptamer in the detection of the thrombin in accordance with the present invention.

In the present invention, the amplification of a fluorescence signal does not occur unless a target protein exists in a sample because of the high selectivity of the DNA aptamer for the target protein (FIG. 3). In a conventional stoichiometric detection method, the detectable amount of a target protein varies depending on the binding strength of the target protein with an aptamer. In contrast, a very small amount of a target protein can be detected by using the signal amplification process of the present invention even when the concentration of the target protein is lower than the dissociation constant of the target protein-aptamer complex. Fluorescence amplification is obtained by the degradation cycle of an F-RNA-Q by RNase H, which is triggered by a small amount of a G-DNA released from the DNA aptamer upon binding to the target protein. For example, thrombin at a concentration of 10 nM, much less than the dissociation constant (~100 nM) of the aptamer-thrombin complex, can be easily detected by using the present invention. The detection of a target protein is achieved very quickly with the method of the present invention compared with the previous aptamer-based detection method employing PCR for signal amplification, which needs additional gel-separation process for quantification of the amplified signal.

The kit provided by the present invention for detecting a target protein in a sample characteristically comprises 1) a DNA duplex consisting of (a) a DNA aptamer and (b) a single-stranded DNA complementary to a region of the DNA aptamer that includes the 5'-extended region; 2) a single-stranded RNA complementary to the G-DNA and labeled with a fluorophore and a quencher; and 3) RNase H.

The target protein may be an antibody, a ligand, a natural compound, a synthetic peptide, a candidate compound for a new drug, or a protein.

The following Examples and Test Examples are given for the purpose of illustration only, and are not intended to limit the scope of the invention. The following examples are included to demonstrate embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain like or similar results without departing from the spirit and scope of the invention.

EXAMPLE 1

Amplification of a Detection Signal of α-Thrombin Using RNase H and an α-Thrombin Aptamer The thrombin aptamer (50 μL, 1 μM) having the nucleotide sequence of SEQ ID NO: 1 was mixed with G-DNA (50 μL, 1 μM) having the nucleotide sequence of SEQ ID NO: 2, followed by addition of RNase H reaction buffer (10×; 50 μL, 500 mM Tris-HCI, pH 8.3, 750 mM KCl, 30 mM $MgCl_2$, and 100 mM dithiothreitol) and RNase-free water (285 μL). The DNA mixture was then heated to 70° C. for 5 min, and slowly cooled down to room temperature to form the duplex. Human α-thrombin (10 μL, final concentration varied: 0, 20, 50, 100 and 200 nM) was added to the preannealed duplex, and the mixture was incubated at 25° C. for 30 min. After addition of F-RNA-Q (50 μL, 1 μm; BIONEER, Korea), which comprises RNA having the nucleotide sequence of SEQ ID NO: 3, labeled with fluorescein and dabcyl, at its 5'- and 3'-ends, respectively, the solutions were incubated with or without RNase H (5 μL, 2.5 unit, New England Biolabs, USA) for specified lengths of time. The fluorescent intensities of the test solutions were measured at varying incubation time (0, 5 and 16 hr) with a Perkin-Elmer LB50B luminescence spectrometer. The above procedure was repeated three times for each concentration of α-thrombin and an average value of the results was calculated (FIG. 2).

As shown in FIG. 2, the increase of the fluorescence intensity was proportional to the concentration of α-thrombin, confirming that the present invention is useful to quantitatively analyze a target protein.

EXAMPLE 2

Selectivity for amplification of a Detection Signal of α-Thrombin Using RNase H and α-Thrombin Aptamer For specificity assessments, the procedure of Example 1 was repeated. BSA, human α-, β-, or γ-thrombin (50 μL, 1 μM) were added to the preannealed DNA duplex. After addition of F-RNA-Q (50 μL, 1 μM), the solutions were incubated with or without RNase H (5 μL, 2.5 unit, New England Biolabs, USA) for 16 hr. Then, the fluorescence intensity of each solution was determined by the method described in Example 1. Each data represents the average value of three independent experiments (FIG. 3).

As shown in FIG. 3, the aptamer selectively binds to the target protein, α-thrombin, with a very high affinity compared with other proteins. This result suggests that the present invention is useful for a selective detection of a target protein.

---

---

What is claimed is:

1. A method of detecting a target protein in a sample, comprising the steps of:

1) forming a DNA duplex consisting of (a) a DNA aptamer comprising a sequence needed for target binding and a sequence extended from the 5'-end of the target binding sequence ("5'-extended region") and (b) a single stranded DNA ("G-DNA") complementary to a region of the DNA aptamer that includes the 5'-extended region;

2) mixing the sample with the DNA duplex of step 1);

3) mixing the mixture obtained in step 2) with RNase H and a single-stranded RNA complementary to the G-DNA, wherein a fluorophore and a quencher are labeled at the 5'- and 3'-ends, respectively, of the single-stranded RNA and wherein the length of the single-stranded RNA is not longer than that of the single-stranded DNA; and 4) measuring the fluorescence intensity of the mixture obtained in step 3) to determine the presence or amount of the target protein in the sample.

2. The method of claim 1, wherein the fluorophore is selected from the group consisting of fluorescein, tetramethylrhodamine, Cy5, Cy3, and Texas Red.

3. The method of claim 1, wherein the quencher is selected from the group consisting of dabsyl, dabcyl, and a black quencher.

4. The method of claim 1, wherein the quencher is a fluorophore which is served as a fluorescence acceptor in fluorescence resonance energy transfer (FRET) mechanism.

5. The method of claim 1, wherein the target protein is an antibody, a ligand, a natural compound, a synthetic peptide or a candidate compound for a new drug.

6. The method of claim 1, wherein the fluorescence intensity is measured by a fluorometer.

7. A kit for detecting a target protein in a sample, comprising 1) a DNA duplex consisting of (a) a DNA aptamer comprising a sequence needed for target binding and a sequence extended from the 5'-end of the target binding sequence ("5'-extended region") and (b) a single-stranded DNA ("G-DNA") complementary to a region of the DNA aptamer that includes the 5'-extended region; 2) a single-stranded RNA complementary to the G-DNA and labeled with a fluorophore and a quencher, wherein the length of the single-stranded RNA is not longer than that of the single-stranded DNA; and 3) RNase H.

8. The kit of claim 7, wherein the fluorophore is selected from the group consisting of fluorescein, tetramethylrhodamine, Cy5, Cy3, and Texas Red.

9. The kit of claim 7, wherein the quencher is selected from the group consisting of dabsyl, dabcyl, and a black quencher.

10. The method of claim 7, wherein the quencher is a fluorophore which is served as a fluorescence acceptor in fluorescence resonance energy transfer (FRET) mechanism.

11. The kit of claim 7, wherein the target protein is an antibody, a ligand, a natural compound, a synthetic peptide, or a candidate compound for a new drug.

* * * * *

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: alpha-thrombin aptamer

<400> SEQUENCE: 1
cactgtggtt ggtgtggttg g                                              21

<210> SEQ ID NO 2
<211> LENGTH: 12
<212> TYPE: DNA
<213> ORGANISM: Artificial Sequence
<220> FEATURE:
<223> OTHER INFORMATION: Guard-DNA complementary to the 1st to 12th
      nucleotides of the alpha-thrombin aptamer of SEQ ID NO:1

<400> SEQUENCE: 2
ccaaccacag tg                                                        12

<210> SEQ ID NO 3
<211> LENGTH: 10
<212> TYPE: RNA
<213> ORGANISM: Artificial Sequence
<220> FEATURE:
<223> OTHER INFORMATION: F-RNA-Q complementary to the 3rd to 12th
      nucleotides of the Guard-DNA of SEQ ID NO:2

<400> SEQUENCE: 3
cacugugguu                                                           10
```